US010456277B2

(12) United States Patent
Quadri

(10) Patent No.: US 10,456,277 B2
(45) Date of Patent: *Oct. 29, 2019

(54) PERCUTANEOUS HEART VALVE

(71) Applicant: Edwards Lifesciences CardiAQ LLC, Irvine, CA (US)

(72) Inventor: Arshad Quadri, West Hartford, CT (US)

(73) Assignee: Edwards Lifesciences CardiAQ LLC, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/984,027

(22) Filed: May 18, 2018

(65) Prior Publication Data
US 2018/0263795 A1   Sep. 20, 2018

Related U.S. Application Data

(63) Continuation of application No. 15/289,834, filed on Oct. 10, 2016, now Pat. No. 9,974,669, which is a
(Continued)

(51) Int. Cl.
*A61F 2/24* (2006.01)
*A61F 2/82* (2013.01)
(Continued)

(52) U.S. Cl.
CPC .............. *A61F 2/82* (2013.01); *A61F 2/2418* (2013.01); *A61F 2/915* (2013.01);
(Continued)

(58) Field of Classification Search
None
See application file for complete search history.

(56) References Cited

U.S. PATENT DOCUMENTS 3,657,744 A  4/1972 Ersek
3,671,979 A  6/1972 Moulopoulos
(Continued)

FOREIGN PATENT DOCUMENTS

CA   2304325 A1   10/2000
CA   2827556 A1   7/2012
(Continued)

OTHER PUBLICATIONS

NJ350: Vote for Your Favorite New Jersey Innovations, Jun. 27, 2014, http://www.kilmerhouse.com/2014/06/nj350-vote-for-your-favorite-new-jersey-innovations/.
(Continued)

*Primary Examiner* — Megan Y Wolf
(74) *Attorney, Agent, or Firm* — Knobbe Martens Olson & Bear LLP

(57) ABSTRACT

A method of delivering a percutaneous heart valve is disclosed. The percutaneous heart valve includes an expandable frame having a plurality of cells and a valve seated inside the expandable frame. The heart valve also includes a proximal anchoring portion and a distal anchoring portion having a plurality of distal anchors. After expansion, the proximal anchoring portion extends distally and a portion of each distal anchor extends proximally. A portion of each distal anchor is positioned radially outwardly from the frame and extends in a direction that is substantially parallel with the longitudinal axis. Proximal portions of the distal anchors are preferably spaced apart by less than two cell lengths from a distal portion of the proximal anchoring portion. During deployment, radial expansion of the frame draws the proximal anchoring portion and the distal anchors into closer proximity with body tissue positioned therebetween.

19 Claims, 12 Drawing Sheets

Related U.S. Application Data continuation of application No. 13/747,270, filed on Jan. 22, 2013, now Pat. No. 9,486,336, which is a continuation of application No. 13/346,593, filed on Jan. 9, 2012, now Pat. No. 9,433,514, which is a continuation of application No. 12/084,586, filed as application No. PCT/US2006/043526 on Nov. 9, 2006, now Pat. No. 8,092,520.

(60) Provisional application No. 60/735,221, filed on Nov. 10, 2005.

(51) Int. Cl.
  *A61F 2/915* (2013.01)
  *A61F 2/848* (2013.01)

(52) U.S. Cl.
  CPC .......... *A61F 2002/8483* (2013.01); *A61F 2002/8486* (2013.01); *A61F 2002/91541* (2013.01); *A61F 2002/91558* (2013.01); *A61F 2220/0016* (2013.01); *A61F 2230/0013* (2013.01); *A61F 2230/0054* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,655,771 A | 4/1987 | Wallsten |
| 4,733,665 A | 3/1988 | Palmaz |
| 4,776,337 A | 10/1988 | Palmaz |
| 4,777,951 A | 10/1988 | Cribier et al. |
| 4,865,600 A | 9/1989 | Carpentier et al. |
| 4,994,077 A | 2/1991 | Dobben |
| 5,197,978 A | 3/1993 | Hess |
| 5,326,371 A | 7/1994 | Love et al. |
| 5,332,402 A | 7/1994 | Teitelbaum |
| 5,370,685 A | 12/1994 | Stevens |
| 5,397,355 A | 3/1995 | Marin et al. |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,554,185 A | 9/1996 | Block et al. |
| 5,575,818 A | 11/1996 | Pinchuk |
| 5,607,444 A | 3/1997 | Lam |
| 5,669,919 A | 9/1997 | Sanders et al. |
| 5,693,061 A | 12/1997 | Pierce et al. |
| 5,697,382 A | 12/1997 | Love et al. |
| D390,957 S | 2/1998 | Fontaine |
| 5,725,519 A | 3/1998 | Penner et al. |
| 5,769,812 A | 6/1998 | Stevens et al. |
| 5,807,398 A | 9/1998 | Shaknovich |
| 5,810,873 A | 9/1998 | Morales |
| 5,855,601 A | 1/1999 | Bessler et al. |
| 5,868,782 A | 2/1999 | Frantzen |
| 5,879,381 A | 3/1999 | Moriuchi et al. |
| 5,902,334 A | 5/1999 | Dwyer et al. |
| 5,935,108 A | 8/1999 | Katoh et al. |
| 5,957,949 A | 9/1999 | Leonhardt et al. |
| 5,992,000 A | 11/1999 | Humphrey et al. |
| 6,004,328 A | 12/1999 | Solar |
| 6,015,431 A | 1/2000 | Thornton et al. |
| 6,042,606 A | 3/2000 | Frantzen |
| 6,053,940 A | 4/2000 | Wijay |
| 6,113,612 A | 9/2000 | Swanson et al. |
| 6,113,631 A | 9/2000 | Jansen |
| 6,132,458 A | 10/2000 | Staehle et al. |
| 6,152,937 A | 11/2000 | Peterson et al. |
| 6,159,237 A | 12/2000 | Alt et al. |
| 6,168,616 B1 | 1/2001 | Brown, III |
| 6,251,093 B1 | 6/2001 | Valley et al. |
| 6,280,466 B1 | 8/2001 | Kugler et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,352,543 B1 | 3/2002 | Cole |
| 6,358,277 B1 | 3/2002 | Duran |
| 6,440,164 B1 | 8/2002 | DiMatteo et al. |
| 6,458,153 B1 | 10/2002 | Bailey et al. |
| 6,475,237 B2 | 11/2002 | Drasler et al. |
| 6,482,228 B1 | 11/2002 | Norred |
| 6,511,491 B2 | 1/2003 | Grudem et al. |
| 6,527,800 B1 | 3/2003 | McGuckin, Jr. et al. |
| 6,602,281 B1 | 8/2003 | Klein |
| 6,610,088 B1 | 8/2003 | Gabbay |
| 6,623,518 B2 | 9/2003 | Thompson et al. |
| 6,629,534 B1 | 10/2003 | St. Goar et al. |
| 6,641,606 B2 | 11/2003 | Ouriel et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,858,034 B1 | 2/2005 | Hijikema et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 7,018,401 B1 | 3/2006 | Hyodoh et al. |
| 7,018,406 B2 | 3/2006 | Seguin et al. |
| 7,044,962 B2 | 5/2006 | Elliott |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| D553,747 S | 10/2007 | Fliedner |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,553,324 B2 | 6/2009 | Andreas et al. |
| 7,569,071 B2 | 8/2009 | Haverkost et al. |
| 7,585,321 B2 | 9/2009 | Cribier |
| 7,608,114 B2 | 10/2009 | Levine et al. |
| 7,615,072 B2 | 11/2009 | Rust et al. |
| 7,621,948 B2 | 11/2009 | Herrmann et al. |
| 7,748,389 B2 | 7/2010 | Salahieh et al. |
| 7,753,949 B2 | 7/2010 | Lamphere et al. |
| D622,387 S | 8/2010 | Igaki |
| D622,388 S | 8/2010 | Igaki |
| 7,771,463 B2 | 8/2010 | Ton et al. |
| 7,785,360 B2 | 8/2010 | Freitag |
| 7,803,185 B2 | 9/2010 | Gabbay |
| 7,806,917 B2 | 10/2010 | Xiao |
| 7,806,919 B2 | 10/2010 | Bloom et al. |

(56) References Cited

U.S. PATENT DOCUMENTS

| | | |
|---|---|---|
| 7,815,589 B2 | 10/2010 | Meade et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| D635,261 S | 3/2011 | Rossi |
| D635,262 S | 3/2011 | Rossi |
| 7,914,569 B2 | 3/2011 | Nguyen et al. |
| 7,981,151 B2 | 7/2011 | Rowe |
| 7,993,392 B2 | 8/2011 | Righini et al. |
| 8,016,877 B2 | 9/2011 | Seguin et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,109,996 B2 | 2/2012 | Stacchino et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,926 B2 | 5/2012 | Hartley et al. |
| 8,167,934 B2 | 5/2012 | Styrc et al. |
| 8,177,799 B2 | 5/2012 | Orban, III |
| 8,182,528 B2 | 5/2012 | Salahieh et al. |
| 8,182,530 B2 | 5/2012 | Huber |
| 8,197,528 B2 | 6/2012 | Colgan et al. |
| 8,216,261 B2 | 7/2012 | Solem |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,482 B2 | 7/2012 | Cottone et al. |
| D665,079 S | 8/2012 | Zago |
| D665,080 S | 8/2012 | Zago |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,052 B2 | 8/2012 | Salahieh et al. |
| 8,303,653 B2 | 11/2012 | Bonhoeffer et al. |
| 8,313,525 B2 | 11/2012 | Tuval et al. |
| 8,317,854 B1 | 11/2012 | Ryan et al. |
| 8,323,335 B2 | 12/2012 | Rowe et al. |
| 8,353,953 B2 | 1/2013 | Giannetti et al. |
| 8,361,137 B2 | 1/2013 | Perouse |
| 8,403,983 B2 | 3/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,449,625 B2 | 5/2013 | Campbell et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,535,368 B2 | 9/2013 | Headley, Jr. et al. |
| 8,562,663 B2 | 10/2013 | Mearns et al. |
| 8,579,963 B2 | 11/2013 | Tabor |
| 8,579,964 B2 | 11/2013 | Lane et al. |
| 8,584,849 B2 | 11/2013 | McCaffrey |
| 8,585,749 B2 | 11/2013 | Shelso |
| 8,617,236 B2 | 12/2013 | Paul et al. |
| 8,640,521 B2 | 2/2014 | Righini et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,672,992 B2 | 3/2014 | Orr |
| 8,679,174 B2 | 3/2014 | Ottma et al. |
| 8,679,404 B2 | 3/2014 | Liburd et al. |
| 8,707,957 B2 | 4/2014 | Callister et al. |
| 8,721,707 B2 | 5/2014 | Boucher et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,753,384 B2 | 6/2014 | Leanna |
| 8,764,818 B2 | 7/2014 | Gregg |
| 8,771,344 B2 | 7/2014 | Tran et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,357 B2 | 8/2014 | Yohanan et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,852,267 B2 | 10/2014 | Cattaneo |
| 8,858,620 B2 | 10/2014 | Salahieh et al. |
| 8,870,947 B2 | 10/2014 | Shaw |
| 8,870,948 B1 | 10/2014 | Erzberger et al. |
| 8,870,950 B2 | 10/2014 | Hacohen |
| 8,876,883 B2 | 11/2014 | Rust |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,939,960 B2 | 1/2015 | Rosenman et al. |
| 8,945,209 B2 | 2/2015 | Bonyuet et al. |
| 8,961,583 B2 | 2/2015 | Hojeibane et al. |
| 8,961,593 B2 | 2/2015 | Bonhoeffer et al. |
| 8,974,524 B2 | 3/2015 | Yeung et al. |
| 8,986,375 B2 | 3/2015 | Garde et al. |
| 8,998,979 B2 | 4/2015 | Seguin et al. |
| 8,998,980 B2 | 4/2015 | Shipley et al. |
| 9,005,270 B2 | 4/2015 | Perkins et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,029,418 B2 | 5/2015 | Dove et al. |
| 9,034,032 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,751 B2 | 7/2015 | Naor |
| 9,173,737 B2 | 11/2015 | Hill et al. |
| 9,180,004 B2 | 11/2015 | Alkhatib |
| 9,186,249 B2 | 11/2015 | Rolando et al. |
| 9,277,990 B2 | 3/2016 | Klima et al. |
| 9,277,993 B2 | 3/2016 | Gamarra et al. |
| 9,295,551 B2 | 3/2016 | Straubinger et al. |
| 9,326,815 B2 | 5/2016 | Watson |
| 9,433,514 B2 * | 9/2016 | Quadri .................. A61F 2/2418 |
| 9,445,897 B2 | 9/2016 | Bishop et al. |
| 9,456,877 B2 | 10/2016 | Weitzner et al. |
| 9,486,336 B2 * | 11/2016 | Quadri .................. A61F 2/2418 |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim et al. |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 9,974,669 B2 * | 5/2018 | Quadri .................. A61F 2/2418 |

(56) References Cited

U.S. PATENT DOCUMENTS

| | | |
|---|---|---|
| 2001/0007956 A1 | 7/2001 | Letac et al. |
| 2001/0047180 A1 | 11/2001 | Grudem et al. |
| 2001/0047200 A1 | 11/2001 | White et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2002/0111619 A1 | 8/2002 | Keast et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0093060 A1 | 5/2004 | Seguin et al. |
| 2004/0117009 A1 | 6/2004 | Cali et al. |
| 2004/0133273 A1 | 7/2004 | Cox |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2004/0243230 A1 | 12/2004 | Navia et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1* | 6/2005 | Salahieh ............... A61F 2/2418 623/2.11 |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2006/0020247 A1 | 1/2006 | Kagan et al. |
| 2006/0020327 A1 | 1/2006 | Lashinski et al. |
| 2006/0052867 A1* | 3/2006 | Revuelta ............... A61F 2/2418 623/2.18 |
| 2006/0058872 A1 | 3/2006 | Salahieh et al. |
| 2006/0095115 A1 | 5/2006 | Bladillah et al. |
| 2006/0116625 A1 | 6/2006 | Renati et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0219620 A1 | 9/2007 | Eells et al. |
| 2007/0250151 A1 | 10/2007 | Pereira |
| 2007/0255394 A1 | 11/2007 | Ryan |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097571 A1 | 4/2008 | Denison et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0125096 A1 | 5/2009 | Chu et al. |
| 2009/0138079 A1 | 5/2009 | Tuval et al. |
| 2009/0149946 A1 | 6/2009 | Dixon |
| 2009/0171438 A1 | 7/2009 | Chuter et al. |
| 2009/0171456 A1 | 7/2009 | Kveen et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2010/0114299 A1 | 5/2010 | Ben Muvhar et al. |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2012/0022639 A1 | 1/2012 | Hacohen et al. |
| 2012/0041550 A1 | 2/2012 | Salahieh et al. |
| 2012/0078360 A1 | 3/2012 | Rafiee |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0259405 A1 | 10/2012 | Weber et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0144375 A1 | 6/2013 | Giasolli et al. |
| 2013/0172983 A1 | 7/2013 | Clerc et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0005764 A1 | 1/2014 | Schroeder |
| 2014/0018912 A1 | 1/2014 | Delaloye et al. |
| 2014/0025163 A1 | 1/2014 | Padala et al. |
| 2014/0046427 A1 | 2/2014 | Michalak |
| 2014/0052237 A1 | 2/2014 | Lane et al. |
| 2014/0067054 A1 | 3/2014 | Chau et al. |
| 2014/0088685 A1 | 3/2014 | Yevzlin et al. |
| 2014/0100651 A1 | 4/2014 | Kheradvar et al. |
| 2014/0155990 A1 | 6/2014 | Nyuli et al. |
| 2014/0163668 A1 | 6/2014 | Rafiee |
| 2014/0172077 A1 | 6/2014 | Bruchman et al. |
| 2014/0194981 A1 | 7/2014 | Menk et al. |
| 2014/0207231 A1 | 7/2014 | Hacohen et al. |
| 2014/0215791 A1 | 8/2014 | Soundararajan et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0257467 A1 | 9/2014 | Lane et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0324160 A1 | 10/2014 | Benichou et al. |
| 2014/0324164 A1 | 10/2014 | Gross et al. |

(56) References Cited

U.S. PATENT DOCUMENTS

| | | |
|---|---|---|
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0331475 A1 | 11/2014 | Duffy et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350666 A1 | 11/2014 | Righini |
| 2014/0350668 A1 | 11/2014 | Delaloye et al. |
| 2014/0358221 A1 | 12/2014 | Ho et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379077 A1 | 12/2014 | Tuval et al. |
| 2015/0005863 A1 | 1/2015 | Para |
| 2015/0005873 A1 | 1/2015 | Chang et al. |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0142103 A1 | 5/2015 | Vidlund |
| 2015/0148731 A1 | 5/2015 | McNamara et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0328001 A1 | 11/2015 | McLean et al. |
| 2015/0335429 A1 | 11/2015 | Morriss et al. |
| 2015/0359629 A1 | 12/2015 | Ganesan et al. |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1369098 A1 | 12/2003 |
| EP | 1472996 A1 | 11/2004 |
| EP | 1259194 B1 | 2/2005 |
| EP | 1734903 A1 | 12/2006 |
| EP | 1255510 B1 | 4/2007 |
| EP | 1827558 A2 | 9/2007 |
| EP | 1239901 B1 | 10/2007 |
| EP | 1935377 B1 | 3/2010 |
| EP | 2238947 A2 | 10/2010 |
| EP | 2308425 A1 | 4/2011 |
| EP | 2398543 A1 | 12/2011 |
| EP | 1281375 B1 | 2/2012 |
| EP | 2496182 A1 | 9/2012 |
| EP | 2319458 B1 | 4/2013 |
| EP | 2124826 B1 | 7/2014 |
| EP | 2750630 A1 | 7/2014 |
| EP | 2967858 A2 | 1/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 5/1919 |
| GB | 2398245 A | 9/1925 |
| GB | 1315844 A | 5/1973 |
| GB | 2245495 A | 1/1992 |
| JP | 2002540889 A | 2/2002 |
| WO | 1997049355 A1 | 12/1997 |
| WO | 0053104 A1 | 9/2000 |
| WO | 0061034 A1 | 10/2000 |
| WO | 0135861 A1 | 5/2001 |
| WO | 0172239 A2 | 10/2001 |
| WO | 03092554 A1 | 11/2003 |
| WO | 2004030569 A2 | 4/2004 |
| WO | 2005011534 A1 | 2/2005 |
| WO | 2005041810 A2 | 5/2005 |
| WO | 2006085304 A2 | 8/2006 |
| WO | 2006089236 A1 | 8/2006 |
| WO | 2007025028 A1 | 3/2007 |
| WO | 2007034488 A2 | 3/2007 |
| WO | 2007058857 A2 | 5/2007 |
| WO | 2007123658 A1 | 11/2007 |
| WO | 2007134290 A2 | 11/2007 |
| WO | 2008005535 A2 | 1/2008 |
| WO | 2008013915 A2 | 1/2008 |
| WO | 2008070797 A2 | 6/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2010004009 A2 | 1/2010 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2012035279 A1 | 3/2012 |
| WO | 2012177942 A2 | 12/2012 |
| WO | 2013028387 A2 | 2/2013 |
| WO | 2013175468 A2 | 11/2013 |
| WO | 2014018432 A2 | 1/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014210124 A1 | 12/2014 |
| WO | 2015077274 A1 | 5/2015 |
| WO | 2015148241 A1 | 10/2015 |

OTHER PUBLICATIONS

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Bavaria, Joseph E. M.D. et al.: "Transcatheter Mitral Valve Implantation: The Future Gold Standard for MR?," Applicant requests the Examiner to consider this reference to be prior art as of Dec. 2010.
European Search Report for EP No. 16202299.0, Completed Mar. 15, 2017.

(56) References Cited

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Raiz, J. Brent, "In3 Company Overview," Jun. 24, 2009.

"Company Overview," at TVT on Jun. 25, 2009.

Ruiz, Carlos E., "Overview of Novel Transcatheter Valve Technologies," Applicant believes this may have been presented on May 27, 2010 at EuroPCR.

"Update," Applicant believes this may have been presented on Jun. 6, 2010 at TVT.

Mack, Michael, M.D., "Antegrade Transcatheter Mitral valve Implantation: A Short-term Experience in Swine Model," Applicant believes this may have been presented on May 2011 at TVT.

Mack, Michael, M.D., "Antegrade Transcatheter Mitral valve Implantation: On-Going Experience in Swine Model," Applicant believes this may have been presented on Nov. 2011 at TCT.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Quadri, Arshad M.D., "Transcatheter Mitral Valve Implantation (TMVI) (An Acute In Vivo Study)," Applicant believes this may have been presented on Sep. 22, 2010 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.

Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.

Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.

Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).

Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

Feldman, Ted, MD. "Prospects for Percutaneous Valve Therapies," Circulation 2007;116:2866-2877. Applicant believes that this may be available as early as Dec. 11, 2007.

(56) References Cited

OTHER PUBLICATIONS

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.

"CardiAQTM Valve Technologies reports Successful First-in-Human Trans-Apical implantation of its Second Generation Transcatheter Mitral Valve," CardiAQ Valve Technologies Press Release, May 20, 2014.

Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.

Neovasc corporate presentation, Oct. 2009, available at http://www.neovasc.com/investors/documents/Neovasc-Corporate-Presentation-October-2009.pdf.

* cited by examiner

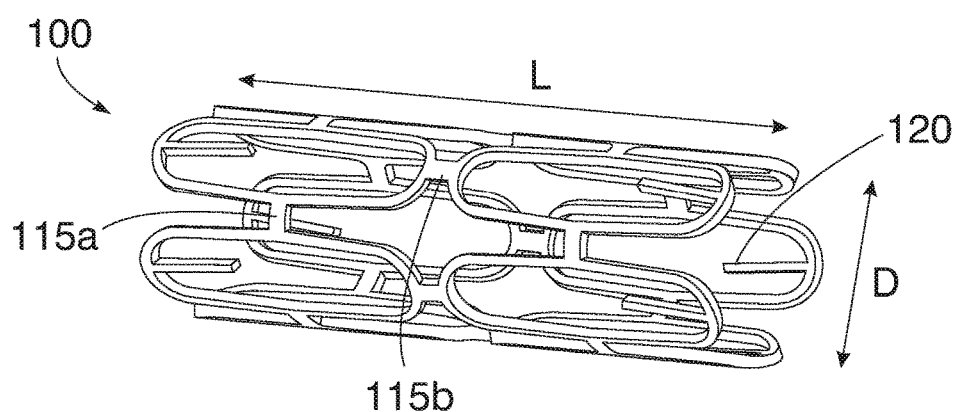
Fig. 3
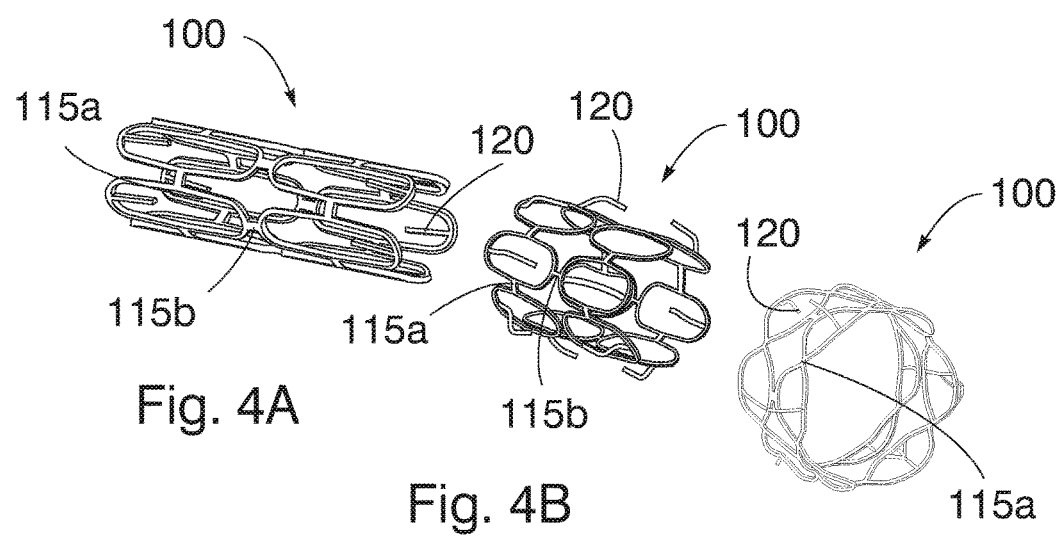
Fig. 4A
Fig. 4B
Fig. 4C

PERCUTANEOUS HEART VALVE

CROSS-REFERENCE TO RELATED APPLICATIONS

This application is a continuation of U.S. application Ser. No. 15/289,834, filed Oct. 10, 2016, now U.S. Pat. No. 9,974,669, which is a continuation of U.S. application Ser. No. 13/747,270, filed Jan. 22, 2013, now U.S. Pat. No. 9,486,336, which is a continuation of U.S. application Ser. No. 13/346,593, filed Jan. 9, 2012, now U.S. Pat. No. 9,433,514, which is a continuation of U.S. application Ser. No. 12/084,586, filed Apr. 13, 2009, now U.S. Pat. No. 8,092,520, which is a national stage of PCT/US2006/043526, filed Nov. 9, 2006, which claims the benefit of U.S. Provisional Application No. 60/735,221, filed Nov. 10, 2005. All of the above applications are incorporated herein by reference in their entirety and are to be considered a part of this specification.

BACKGROUND

Field of the Invention

The present invention relates to a vascular balloon-expandable and/or self-expanding stent that can be used as a connecting/attaching mechanism for various kinds of vascular grafts or other prostheses in the vascular system of the human body.

SUMMARY OF THE INVENTION

It is a primary object of the present invention to provide a vascular balloon-expandable and/or self-expanding stent to facilitate efficient execution of simple and more complex vascular and cardiac procedures by less invasive and/or percutaneous techniques.

This and other objects of the present invention are achieved by an expandable vascular stent comprising an m×n array of ovals formed into a cylinder having a diameter, a circumference, an axis, and a length in the direction of the axis, where m is the number of columns of ovals in the circumferential direction and n is the number of rows of ovals in the axial direction. Connecting means located at rows 1 and n of the m×n array connect the cylinder to a surrounding body. The array of ovals can be of any size and number in a given stent.

The ovals have a short axis and a long axis, the short axis of the ovals extending in the circumferential direction and the long axis of the ovals extending in the axial direction. The cylinder is expandable from an initial diameter to a pre-determined final diameter, wherein an increase in the diameter of the stent results in a substantial decrease in the length of the stent to bring the prongs together to produce a connection to the body surrounding the stent.

The connecting means comprise a plurality of prongs extending inwardly from the outer ends of respective ovals in rows 1 and n of the m×n array. The prongs are arranged in facing pairs extending from ovals that are in alignment in the axial direction, and are approximately collinear in ovals having a common long axis, and approximately parallel in ovals having a common short axis.

Prior to expansion of the cylinder, the prongs substantially conform to the shape of the cylinder. As the stent expands, the distance between the prongs decreases and the prongs extend outwardly from the cylinder to engage the surrounding tissue.

Circumferential connectors connect adjacent ovals to each other in the circumferential direction and axial connectors connecting adjacent ovals to each other in the axial direction. The circumferential connectors and the axial connectors are positioned between the ovals coincident with the common short and long axes of the ovals, respectively.

The tube and the prongs can be made of surgical stainless steel, the tube being expandable using an angioplasty balloon; or the tube and the prongs can be made of a memory metal and the tube is self-expanding.

Other objects, features, and advantages of the present invention will be apparent to those skilled in the art upon a reading of this specification including the accompanying drawings.

Disclosed herein are embodiments a method of deploying a percutaneous heart valve into a body cavity having an opening surrounded by surrounding body tissue, the method comprising delivering a percutaneous heart valve to the body cavity in a collapsed configuration, the percutaneous heart valve comprising an expandable frame comprising a proximal end and a distal end and a longitudinal axis extending therethrough, the expandable frame comprising a plurality of cells configured to permit the frame to radially expand and collapse between the collapsed configuration and an expanded configuration, a valve seated inside the expandable frame, a proximal anchoring portion, and a distal anchoring portion comprising a plurality of distal anchors, and radially expanding the expandable frame to the expanded configuration within the opening, wherein, when the percutaneous heart valve is in the expanded configuration the proximal anchoring portion extends at least partially distally, at least a portion of each distal anchor extends proximally to a proximalmost portion of the distal anchor positioned radially outward from the frame, the proximalmost portions extending in a direction that is more parallel with the longitudinal axis than with a transverse axis perpendicular to the longitudinal axis, at least one of the plurality of distal anchors bends radially outwardly before bending to extend toward the proximal anchoring portion, and the proximalmost portions of the plurality of distal anchors are spaced apart by less than two cell lengths from a distalmost portion of the proximal anchoring portion, wherein radially expanding the expandable frame draws the proximal anchoring portion and the plurality of distal anchors closer together with the surrounding body tissue positioned between the proximal anchoring portion and the plurality of distal anchors. In some embodiments, when the frame is in the expanded configuration within the opening, the proximal anchoring portion is positioned on a first side of the surrounding body tissue and the distal anchors are positioned on a second side of the surrounding body tissue opposite the first side, and upon movement of the frame within the opening in a proximal direction, the distal anchors longitudinally engage the second side of the surrounding body tissue with a proximally-facing surface of the proximalmost portions of the distal anchors which are positioned radially outward from the frame. In some embodiments, when the frame is in the expanded configuration within the opening the proximal anchoring portion is positioned on a first side of the surrounding body tissue and the distal anchors are positioned on a second side of the surrounding body tissue opposite the first side, and the proximalmost portions of the distal anchors engage the second side of the surrounding body tissue at a location radially outward of the opening. In some embodiments, the proximal anchoring portion comprises a plurality of circumferentially spaced anchoring tips positioned radially outward from the frame when the frame is in the expanded configuration. In some embodiments, when the frame is in the expanded configuration within the opening, the plurality of circumferentially spaced anchoring tips of the proximal anchoring portion extend at least partially distally toward a first side of the surrounding body tissue. In some embodiments, the method can further comprising forming the cells, the proximal anchoring portion, and the distal anchoring portion by laser cutting. In some embodiments, each of the plurality of distal anchors are connected to distal ends of cells of the frame. In some embodiments, when the frame is in the expanded configuration, the distal ends of each cell to which the distal anchors are attached are in a position spaced radially outward relative to a portion of the frame located proximal to the distal ends of each cell to which the distal anchors are attached. In some embodiments, when the frame is in the expanded configuration, the plurality of distal anchors bend radially outwardly to a position spaced radially outward relative to a portion of the frame located proximal to the distal ends of the cells to which the distal anchors are attached, the at least one distal anchor being attached to the distal end of the cell, at least a portion of the at least one distal anchor extending generally parallel to the longitudinal axis. In some embodiments, a distalmost portion of the proximal anchoring portion and the proximalmost portions of the plurality of distal anchors are sized to pinch first and second sides of the surrounding body tissue together after the radially expanding. In some embodiments, the body cavity comprises a native aortic valve.

Also disclosed herein are embodiments of a method of deploying a percutaneous heart valve within a body cavity having an opening surrounded by surrounding body tissue, the method comprising delivering a percutaneous heart valve to the body cavity in a collapsed configuration, the percutaneous heart valve comprising an expandable frame comprising a proximal end and a distal end and a longitudinal axis extending therethrough, the expandable frame comprising a plurality of cells configured to permit the frame to radially expand and collapse for deployment within the opening of the body cavity between the collapsed configuration and an expanded configuration, a valve seated inside the expandable frame, a proximal anchoring portion, and a distal anchoring portion comprising a plurality of distal anchors, each distal anchor comprising an attached end connected to the frame, a free end, and a bend between the attached end and the free end, and radially expanding the expandable frame to the expanded configuration within the opening, wherein, when the percutaneous heart valve is in the expanded configuration the proximal anchoring portion extends at least partially distally, at least a portion of each distal anchor extends proximally to a proximalmost portion of the distal anchor positioned radially outward from the frame, the proximalmost portions extending in a direction that is more parallel with the longitudinal axis than with a transverse axis perpendicular to the longitudinal axis, and the proximalmost portions of the distal anchors are spaced apart by less than two cell lengths from a distalmost portion of the proximal anchoring portion, wherein the radially expanding the expandable frame draws the proximal anchoring portion and the distal anchors closer together with the surrounding body tissue positioned between the proximal anchoring portion and the plurality of distal anchors. In some embodiments, when the frame is in the expanded configuration, at least a portion of the distal anchors between the attached end and the bend extends radially outward. In some embodiments, when the frame is in the expanded configuration, the bend orients a portion of the distal anchor immediately after the bend in a direction more parallel with the longitudinal axis than a portion of the distal anchor immediately before the bend. In some embodiments, when the frame is in an expanded configuration within the opening, the proximal anchoring portion is positioned on a first side of the surrounding body tissue and the distal anchors are positioned on a second side of the surrounding body tissue opposite the first side, and upon movement of the frame within the opening in a proximal direction, the plurality of distal anchors longitudinally engage the second side of the surrounding body tissue with a proximally-facing surface of the proximalmost portions of the distal anchors which are positioned radially outward from the frame. In some embodiments, when the frame is in the expanded configuration within the opening the proximal anchoring portion is positioned on a first side of the surrounding body tissue and the plurality of distal anchors are positioned on a second side of the surrounding body tissue opposite the first side, and the proximalmost portions of the plurality of distal anchors engage the second side of the surrounding body tissue at a location radially outward of the opening. In some embodiments, the proximal anchoring portion comprises a plurality of circumferentially spaced anchoring tips positioned radially outward from the frame when the frame is in an expanded configuration. In some embodiments, when the frame is in the expanded configuration within the opening, the plurality of circumferentially spaced anchoring tips of the proximal anchoring portion extend at least partially distally toward a first side of the surrounding body tissue. In some embodiments, the body cavity comprises a native aortic valve.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 3 shows the stent form of FIG. 1 rolled into a stent.

FIGS. 4A-4C show the progression of deformation of the stent of FIG. 3 as it is stretched radially along its diameter.

DETAILED DESCRIPTION OF THE PREFERRED EMBODIMENTS

Figure 1:
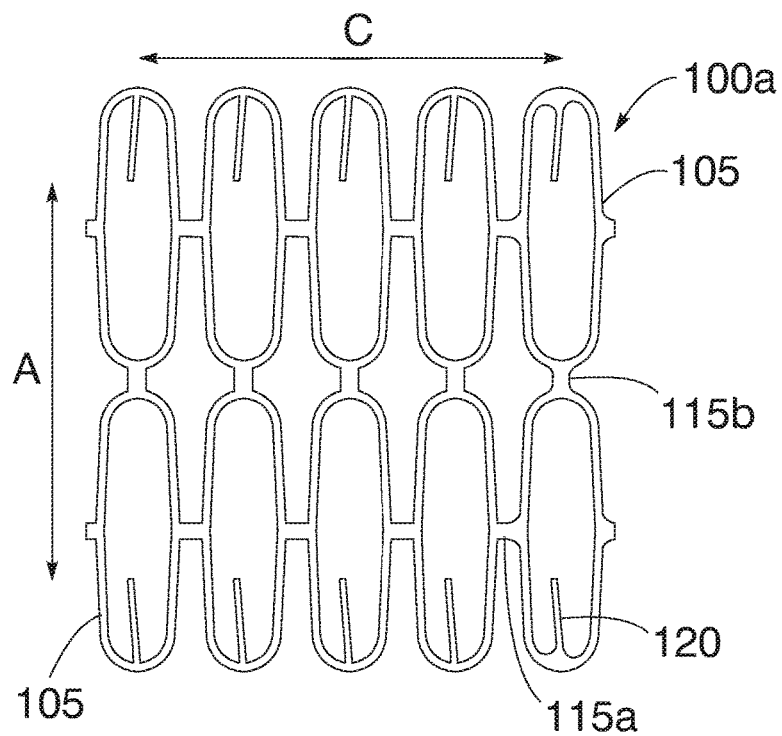
FIG. 1 shows a first embodiment of a stent form stamped from a piece of metal.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

As shown in FIGS. 3 and 4A-4C, a first embodiment of the device is a balloon expandable stainless steel stent 100 that can be expanded from an initial diameter (shown in FIG. 4A) to a pre-determined final diameter (shown in FIG. 4C) depending on the set dimensions of the balloon used to expand it. The configuration of the stent 100 is such that, with reference to FIG. 3, an increase in the diameter (D) of the stent will result in a substantial decrease in the length (L) of the stent.

To achieve this change in the shape and dimension of the stent 100, an m×n array 100a of ovals 105 is formed as shown in FIG. 1, where m is the number of columns of ovals in the circumferential direction C and n is the number of rows of ovals in the axial, or lengthwise, direction A, and where the short axis of the ovals 105 extends in the circumferential direction C and the long axis of the ovals 105 extends in the axial direction A. The array 100a shown in FIG. 1 is a 2×5 array. However, the array 100a can be any size greater than 1×1, depending on the desired size of the circumference and the length of the stent.

Figure 2:
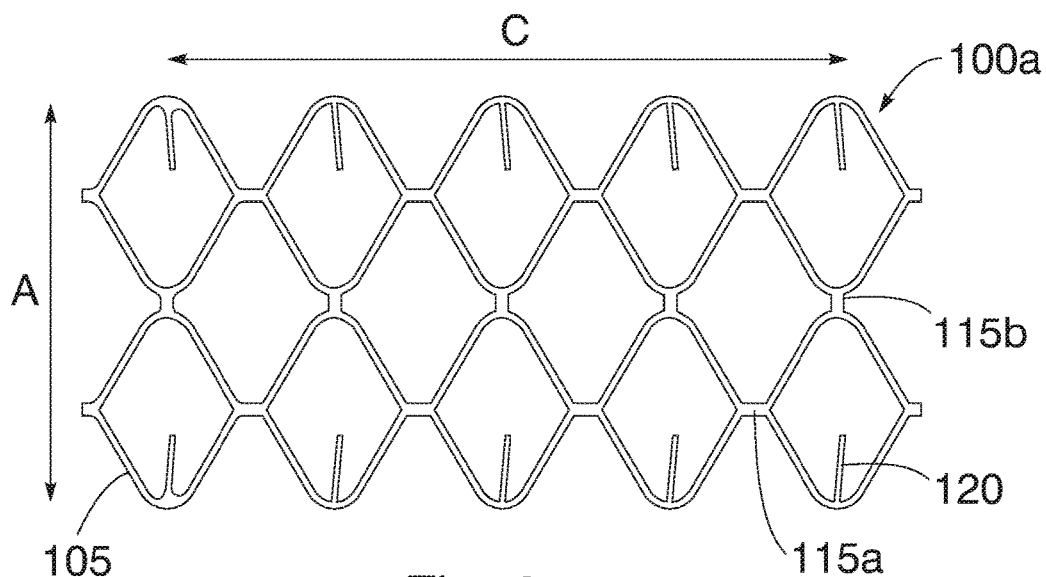
FIG. 2 shows the stent form of FIG. 1 stretched widthwise.

With reference to FIGS. 1 and 2, the array 100a of ovals 105 can be formed by stamping or electrical discharge machining from a sheet or tube of metal, preferably stainless steel. Adjacent ovals 105 are connected to each other in the circumferential direction C by connectors 115a and in the axial direction A by connectors 115b positioned between the ovals coincident with their common short and long axes, respectively.

At least some of the ovals 105 at the ends of the stent 100 (that is, the ovals 105 in rows 1 and n in the axial direction) have a prong 120 extending inwardly from their outer ends in approximate alignment with their longitudinal axes. The prongs 120 are placed in facing pairs extending from ovals 105 that are in alignment in the axial direction A. Thus, for ovals 105 having a common long axis, the prongs 120 are approximately collinear; while for ovals 105 having a common short axis, the prongs 120 are approximately parallel.

There may be intervening "blank" ovals 105 without any prongs 120, and which serve merely as spacers. The blank ovals 105 are utilized in some situations where more space is required between the connecting prongs 120.

If the array 100a of ovals 105 is formed from a sheet of metal, then the array 100a is rolled into a cylinder. The rolled cylinder and the stamped or machined tube have the general configuration of a stent 100, as shown in FIG. 4A, with the longitudinal axis of the cylinder being parallel to the long axes of the ovals 105.

In this embodiment, the prongs 120 are pre-bent. That is, at the time the stent 100 is formed, the prongs 120 are bent outwardly relative to the longitudinal axis of the cylinder, adjacent their attached ends, and also are bent inwardly relative to the longitudinal axis of the cylinder at a point offset from their free ends, in a reverse curve, so as to have a hook configuration.

An angioplasty balloon 130 is used to expand the undeployed stent 100 and to post the expanded stent 100 in the wall of an artery or other body cavity. When the balloon 130 is inflated, the ovals 105 expand in the direction of their short axes and contract along the direction of their long axes, deforming the ovals 105 into diamonds and causing a reduction in the length of the stent 100, as shown in FIGS. 4B and 4C. As also shown in FIGS. 4B and 4C, the deformation of the ovals 105 also causes the approximately collinear prongs 120 to draw closer together to engage the surrounding tissue and the approximately parallel prongs 120 to spread farther apart. This deformation of the ovals 105 and movement of the prongs 120 provide the connecting mechanism of the stent 100.

The angioplasty balloon 130 is the correct size and shape to expand the stent 100 to the desired size and shape. The undeployed stent 100 is loaded over the balloon 130 of a conventional balloon catheter 132 and inserted into the artery or other body cavity according to conventional medical procedure. Inflating the balloon 130 deploys (opens) the stent 100 (that is, causes an increase in its diameter and a decrease in its length), which remains expanded to keep the artery or body cavity open. A high-pressure balloon 130 allows the physician to fully expand the stent 100 until it is in full contact with the wall of the artery or body cavity. A low compliance balloon 130 is used so that the stent 100 and the artery or body cavity will not be over-expanded, and so that the balloon 130 will not dog-bone and over-expand the artery or body cavity on either end of the stent 100. The stent 100 stays in position after the balloon 130 is deflated and removed from the body.

In instances when the stent 100 is self-expanding, i.e. made from memory metal, then upon deployment the stent 100 takes its predetermined configuration.

Figure 5A:
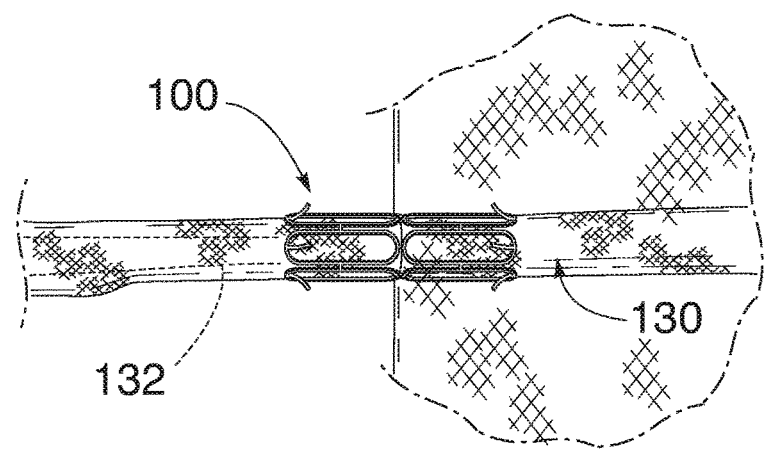
FIGS. 5A-5Q show the steps in the expansion of the stent of FIG. 3 in an artery or other body cavity.
Figure 5B:
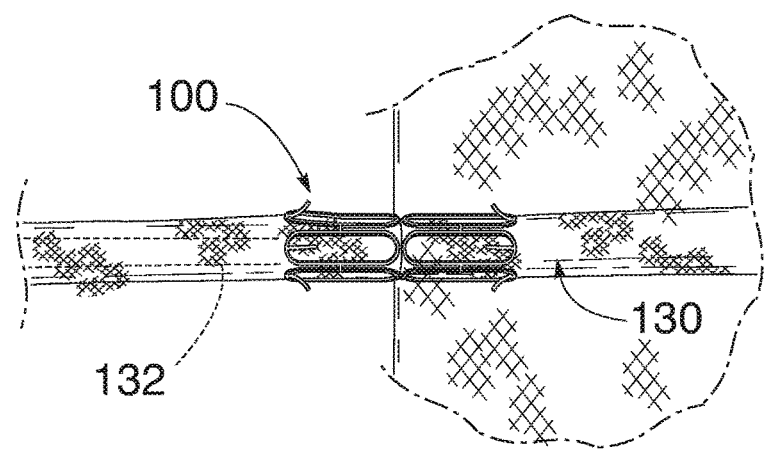
Figure 5C:
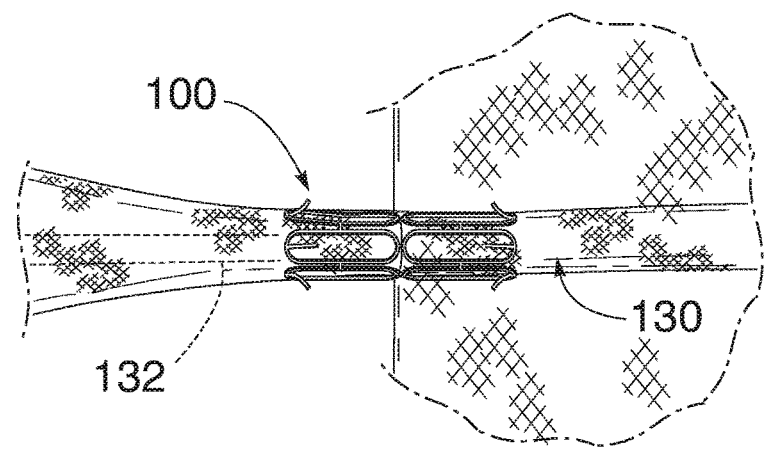
Figure 5D:
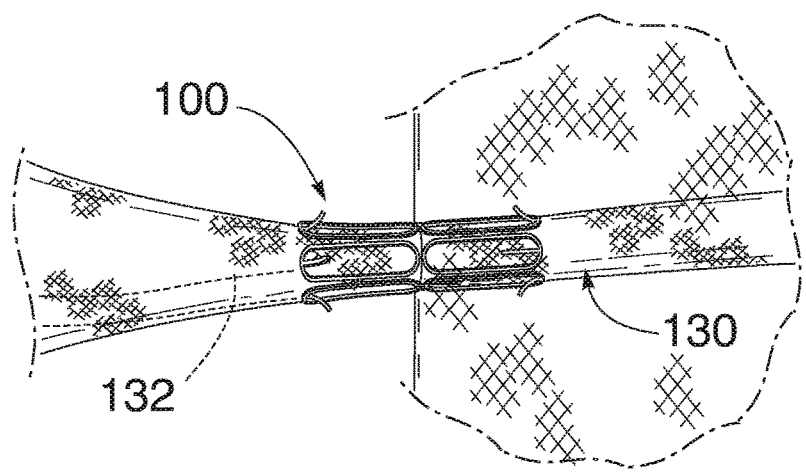
Figure 5E:
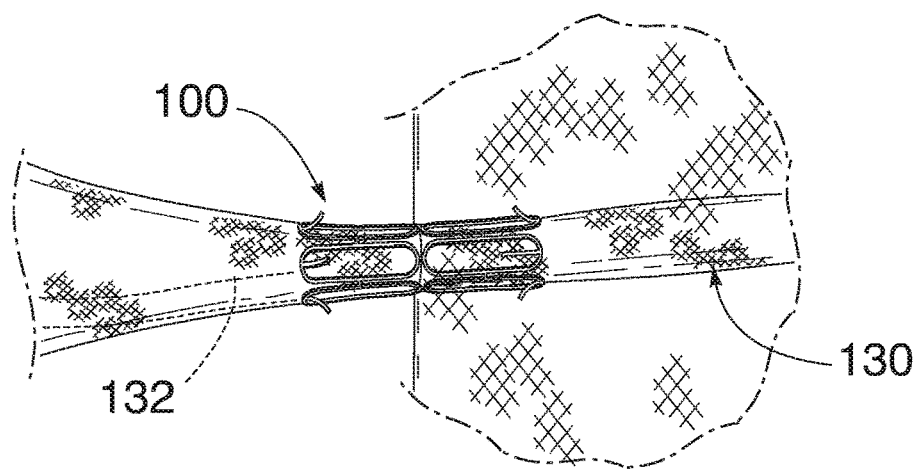
Figure 5F:
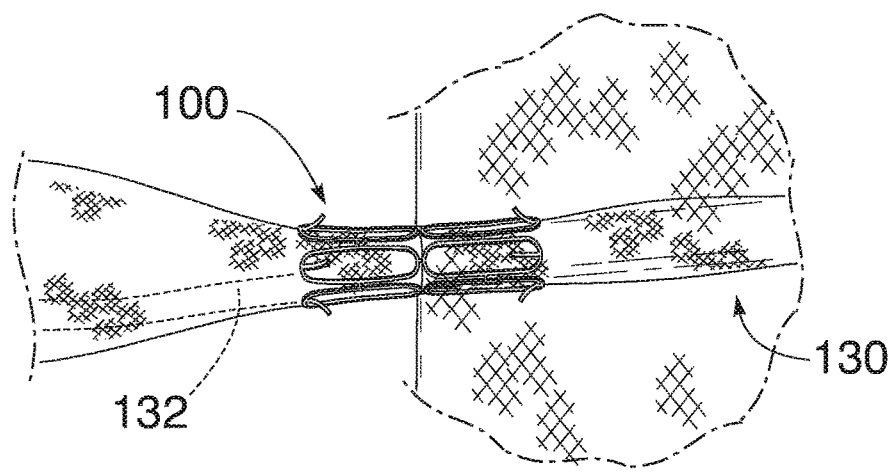
Figure 5G:
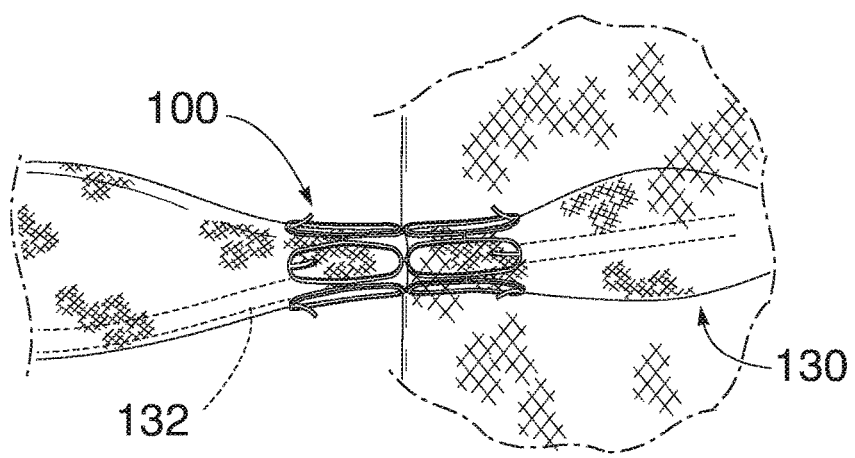
Figure 5H:
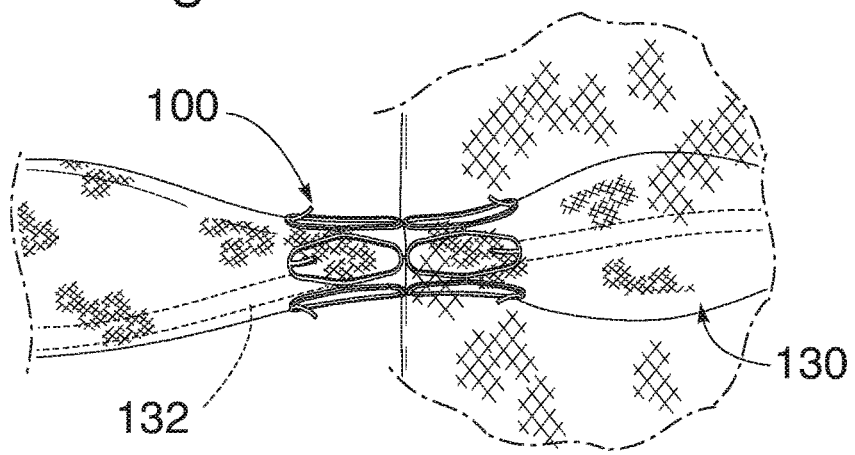
Figure 5I:
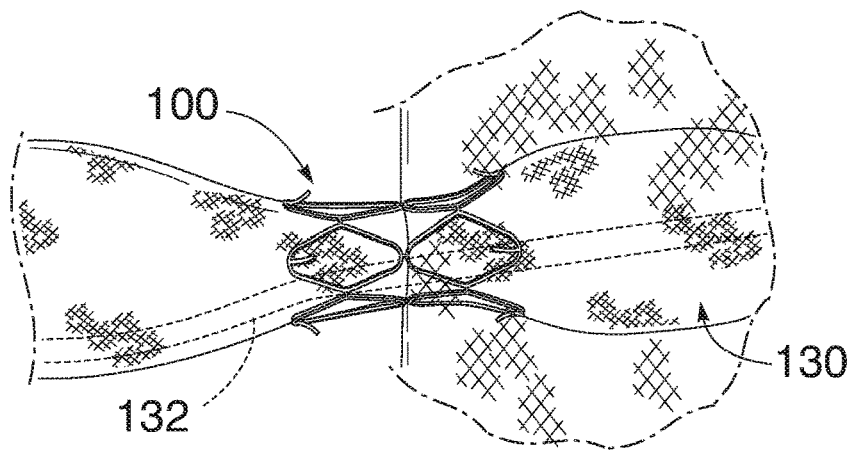
Figure 5J:
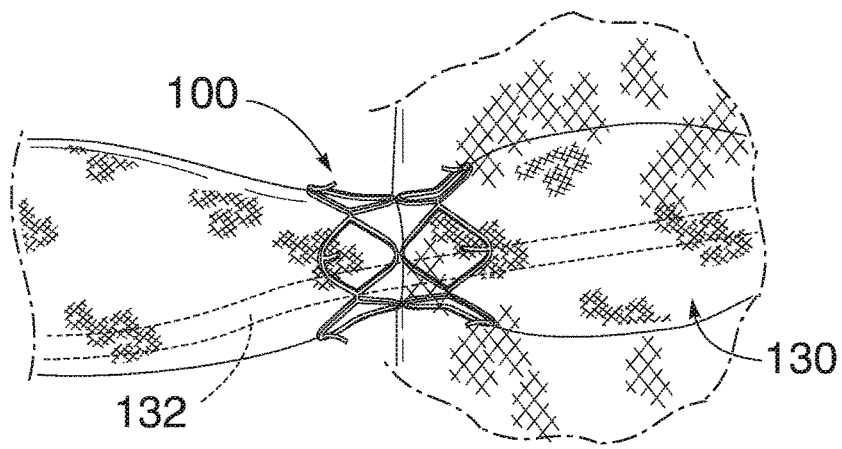
Figure 5K:
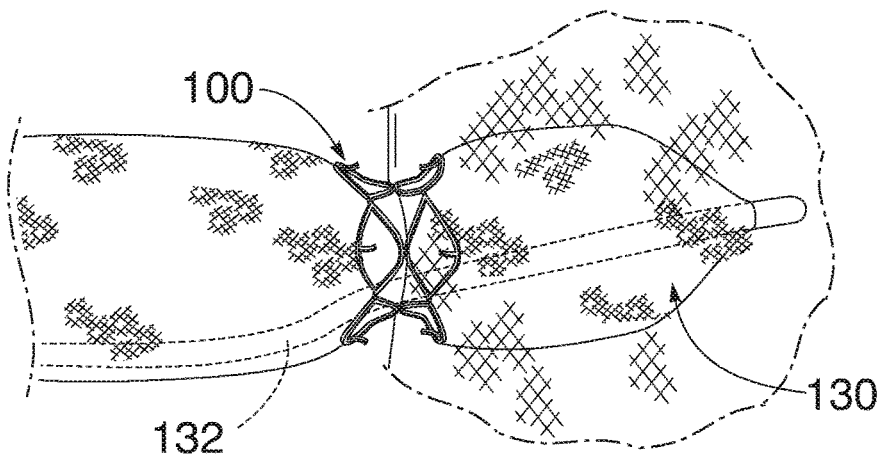
Figure 5L:
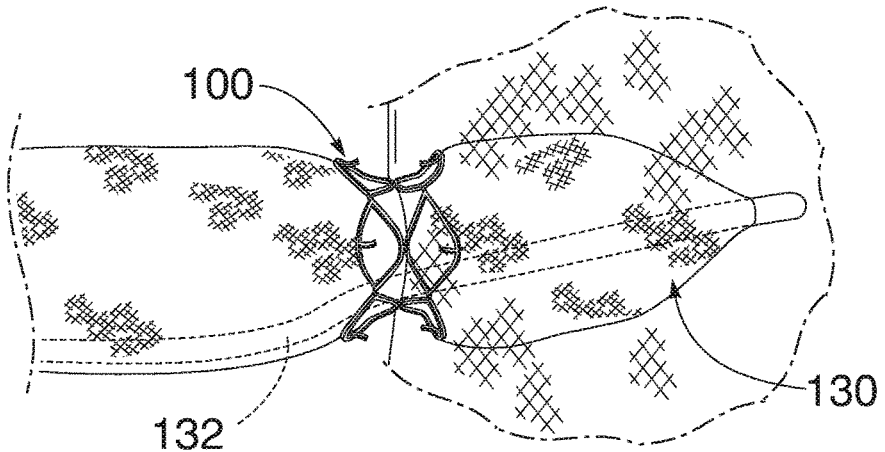
Figure 5M:
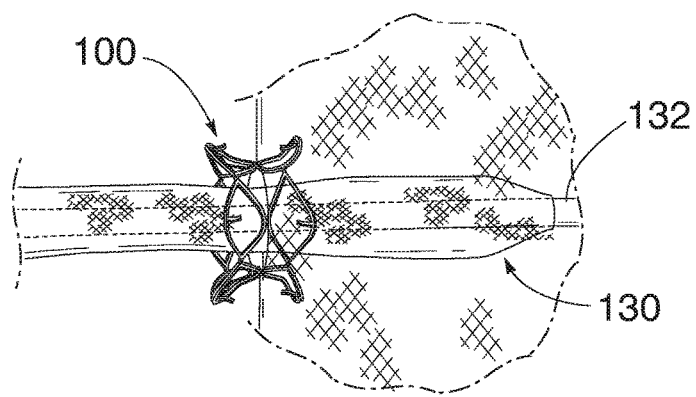
Figure 5N:
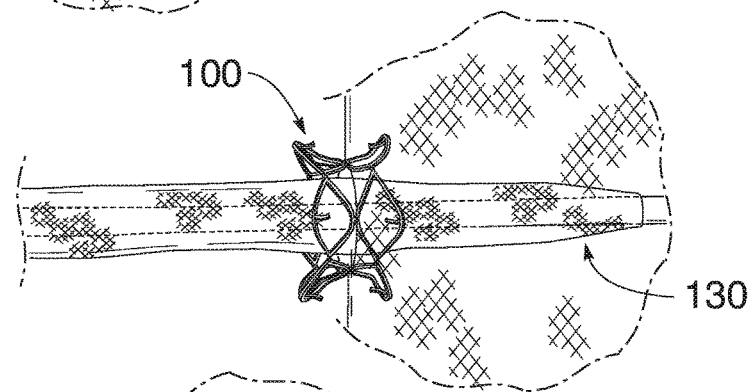
Figure 5O:
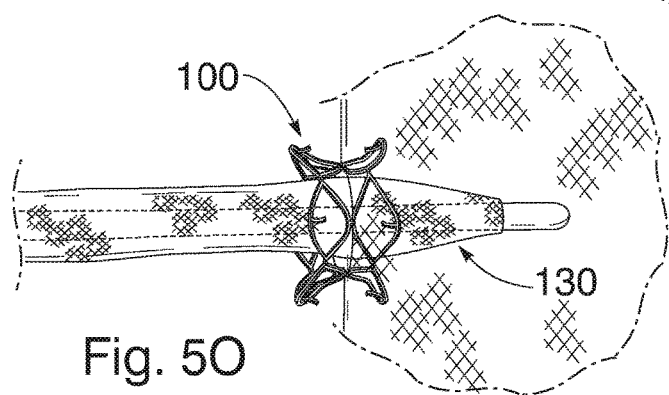
Figure 5P:
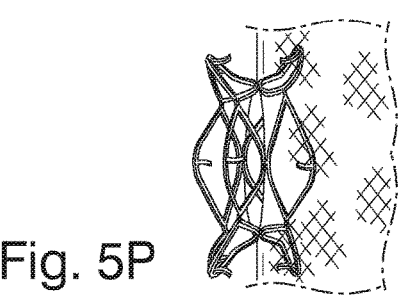
Figure 5Q:
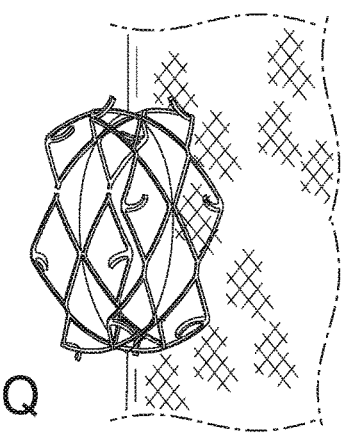

FIGS. 5A-5Q show the steps in the expansion of the stent of FIG. 3 in an artery or other body cavity.

The stent 100 in accordance with the present invention can also be of use as a versatile connector in clinical settings in which it can be pre-attached to a side wall of another prosthesis, such as an endo-luminal graft. It can also be used as a connector to connect main and branch endo-aortic grafts for branch graft repair, as described in my U.S. patent application Ser. No. 10/960,296, filed Oct. 8, 2004.

The stent 100 in accordance with the present invention can further be used in conjunction with percutaneous heart valve technology. In a percutaneous heart valve procedure, a collapsed percutaneous heart valve 125 is mounted on a balloon-expandable stent 100 and threaded through the patient's circulatory system via a catheter to the aortic valve from either an antegrade approach (in which the patient's septum and mitral valve are crossed to reach their native aortic valve) or a retrograde approach (in which the percutaneous heart valve 125 is delivered directly to the aortic valve through the patient's main artery). Once in the aortic valve, the percutaneous heart valve 125 is expanded by a balloon catheter to push the patient's existing valve leaflets aside and anchor inside the valve opening.

Figure 6A:
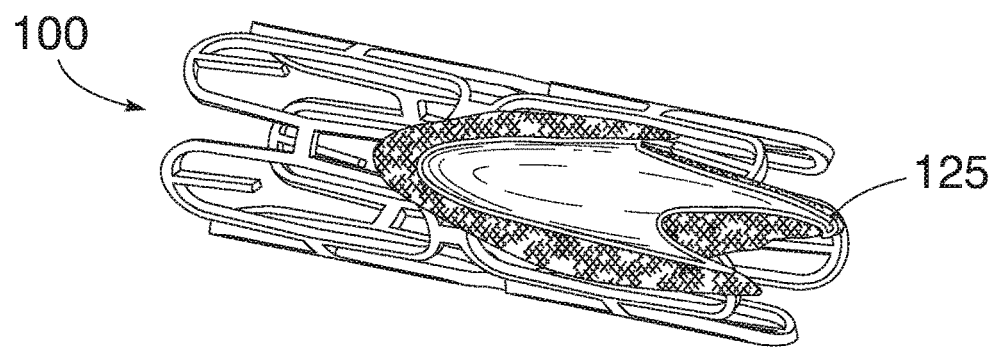
FIG. 6A is a perspective view, partially cut away, of a collapsed prosthetic heart valve loaded in an undeployed stent in accordance with the present invention.
Figure 6B:
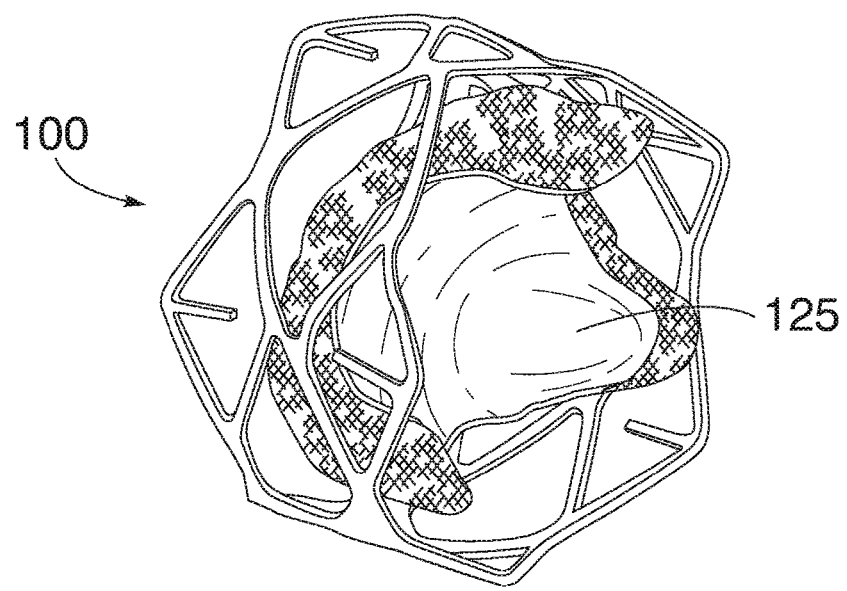
FIG. 6B is a perspective view, partially cut away, of the prosthetic heart valve and stent of FIG. 6A in their expanded conditions.

As shown in FIG. 6A, the percutaneous heart valve 125 in a collapsed state can be seated inside the undeployed stent 100 in accordance with the present invention, which in turn is loaded over the balloon of a conventional balloon catheter, as previously described. Once the valve 125 and stent 100 are positioned in the desired location, the balloon 130 is inflated, causing the valve 125 and the stent 100 to expand, as shown in FIG. 6B. The valve 125 is fixed in position by the mechanism provided by the stent 100.

Figure 7A:
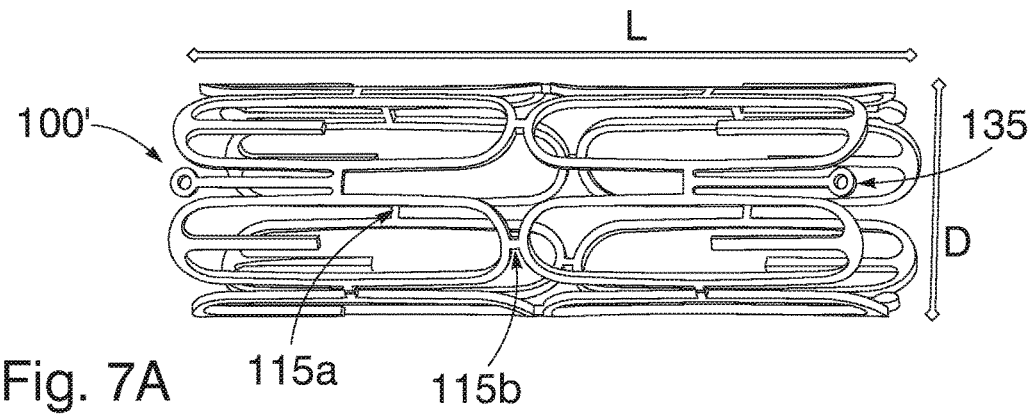
FIGS. 7A-7C show the progression of deformation of a second embodiment of the stent as it is stretched radially along its diameter.
Figure 7B:
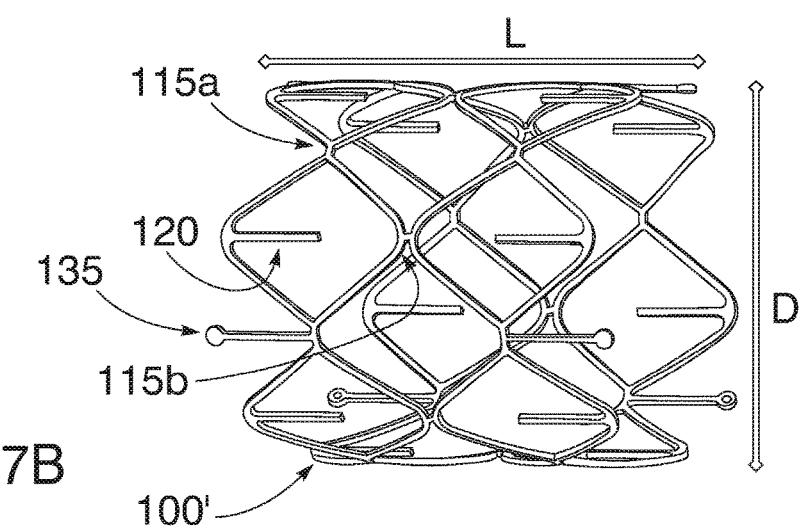
Figure 7C:
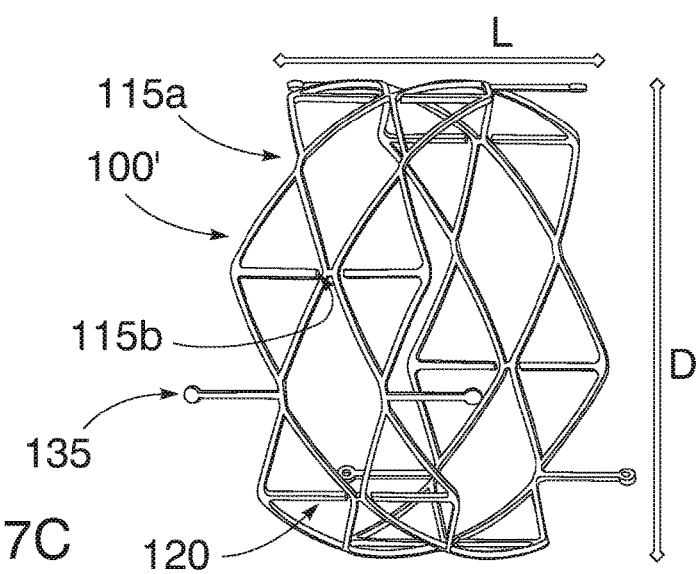

A second embodiment of the stent 100', and the progression of its deformation as it is stretched radially along its diameter, is shown in FIGS. 7A-7C. In this alternate embodiment, the stent 100' is similar to the stent 100, but has additional prongs 135 extending from and perpendicular to the connectors 115a positioned between the ovals 105, and parallel to the longitudinal axis of the stent 100'. These prongs 135 are for the purpose of attaching the stent 100' to, for example, a branch graft or a valve.

Figure 8A:
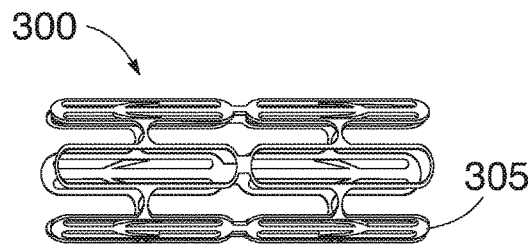
FIG. 8A is a side elevational view of a third embodiment of the stent.
Figure 8C:
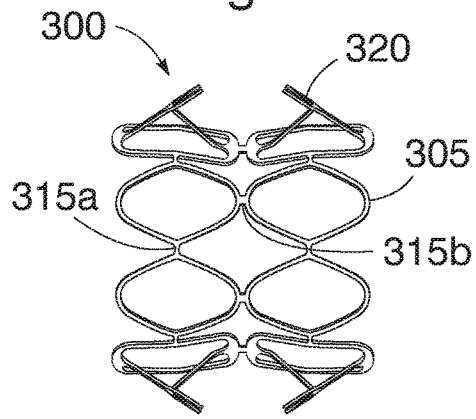
FIG. 8C is a side elevational view of the stent of FIG. 8A in a deformed state after being stretched radially along its diameter.
Figure 8B:
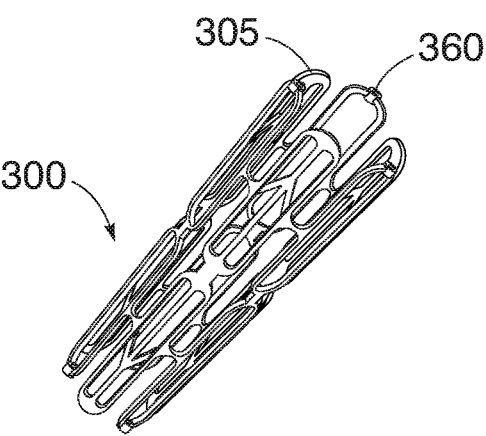
FIG. 8B is a perspective view of the stent of FIG. 8A.
Figure 8D:
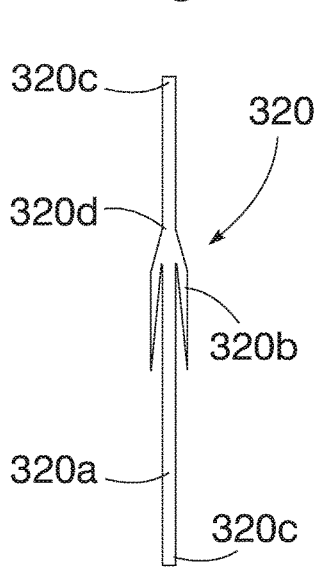
FIG. 8D is an enlarged view of a prong of the stent of FIG. 8A.
Figure 8E:
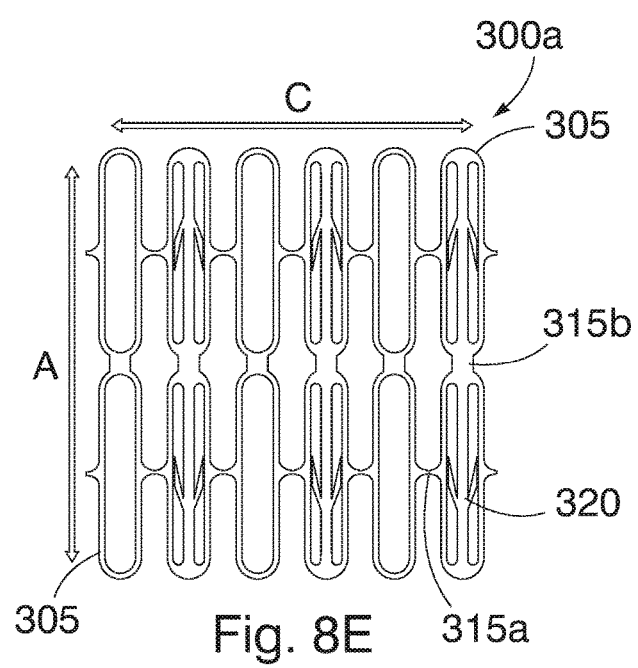
FIG. 8E is a plan view of the stent form of FIG. 8A.

A third embodiment of the stent 300 is shown in its undeployed state in FIGS. 8A and 8B, and in its deployed state after being stretched radially along its diameter in FIG. 8C. In the third embodiment, the stent 300 is formed of an m×n array 300a of ovals 305 formed as shown in FIG. 8E. With reference to FIG. 8D, the array 300a of ovals 305 can be formed by laser-cutting a sheet or tube of metal, preferably stainless steel or a memory metal. Adjacent ovals 305 are connected to each other in the circumferential direction C by connectors 315a and in the axial direction A by connectors 315b positioned between the ovals coincident with their common short and long axes, respectively.

At least some of the ovals 305 at the ends of the stent 300 (that is, the ovals 305 in rows 1 and n in the axial direction) have a prong 320 extending inwardly from their outer ends in approximate alignment with their longitudinal axes. The prongs 320 are placed in facing pairs extending from ovals 305 that are in alignment in the axial direction A. Thus, for ovals 305 having a common long axis, the prongs 320 are approximately collinear; while for ovals 305 having a common short axis, the prongs 320 are approximately parallel. The prongs 350 are bifurcated, providing two point penetration for better purchase.

Referring now to FIGS. 8D and 8E, in the embodiment of FIGS. 8A-8C, each prong 320 includes a spine 320a extending the length of the long axis of the oval 305 and a furcation 320b on either side of the spine 320a at a location between the ends of the spine 320. The spine 320a has two end hinge points 320c at the ends thereof and one intermediate hinge point 320d at the base of the furcations 320b. The amount by which the ovals 305 are foreshortened and the angle of the prongs 320 (that is, the angle of the furcations 320b) can be adjusted by varying the location of the furcations 320b and the intermediate hinge point 320d relative to the ends of the spines 320 and the end hinge points 320c.

There may be intervening "blank" ovals 305 without any prongs 320, and which serve merely as spacers. The blank ovals 305 are utilized in some situations where more space is required between the connecting prongs 320. At least some of the ovals 305 at one end of the stent 300 can include a docking socket 360 (shown in FIG. 8C) for mating to the cardiac locking pin of a valve frame.

Figure 9A:
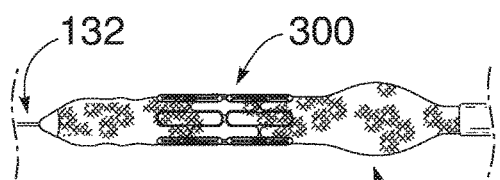
FIGS. 9A-9G show the steps in the expansion of the stent of FIG. 8A in an artery or other body cavity.
Figure 9B:
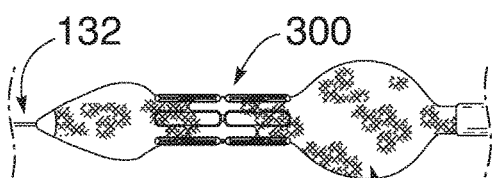
Figure 9C:
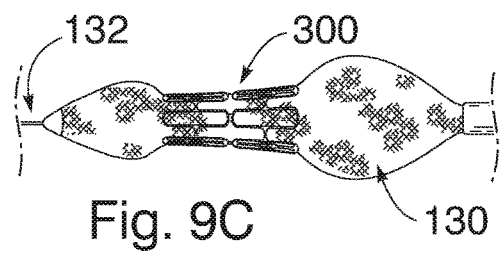
Figure 9D:
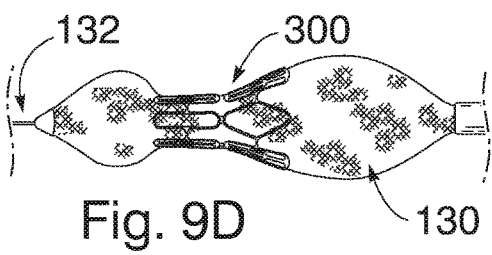
Figure 9E:
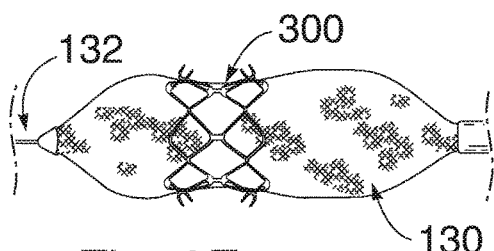
Figure 9F:
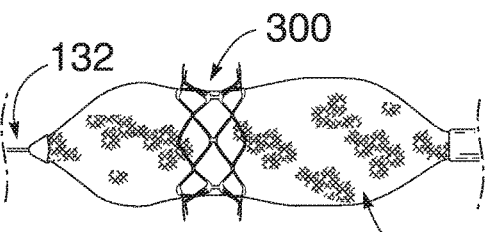
Figure 9G:
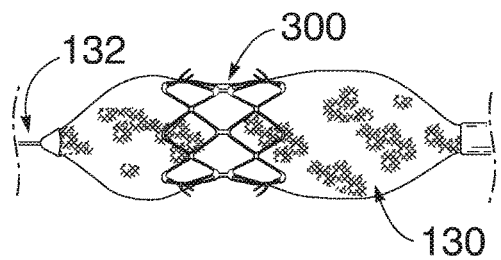

FIGS. 9A-5Q show the steps in the expansion of the stent of FIGS. 8A-8C in an artery or other body cavity, using an angioplasty balloon. The undeployed stent 300 is loaded over the balloon 130 of a conventional balloon catheter 132 and inserted into the artery or other body cavity according to conventional medical procedure. As the balloon 130 inflates, the ovals 305 foreshorten in the axial direction, causing the spines 320a of the prongs 320 to bend at the hinges 320c and 320d and the consequent activation of the prongs 320. As the balloon 130 continues to inflate, the angles assumed by the spines 320a at their hinges reach their maximums, bringing opposing furcations 320b together to engage the tissue therebetween.

Figure 10A:
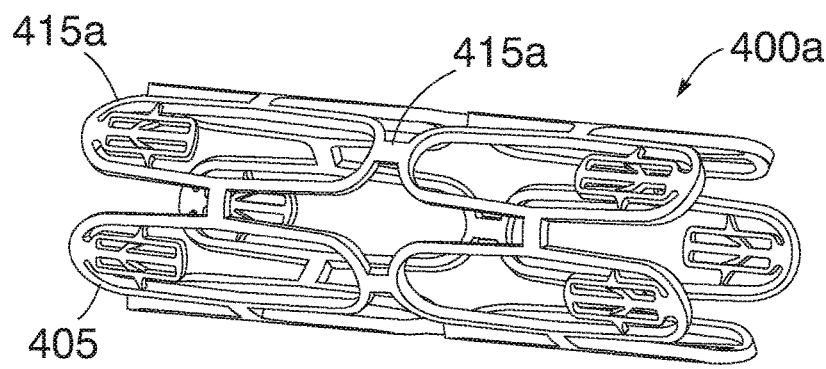
FIG. 10A is a perspective view of a fourth embodiment of the stent.
Figure 10B:
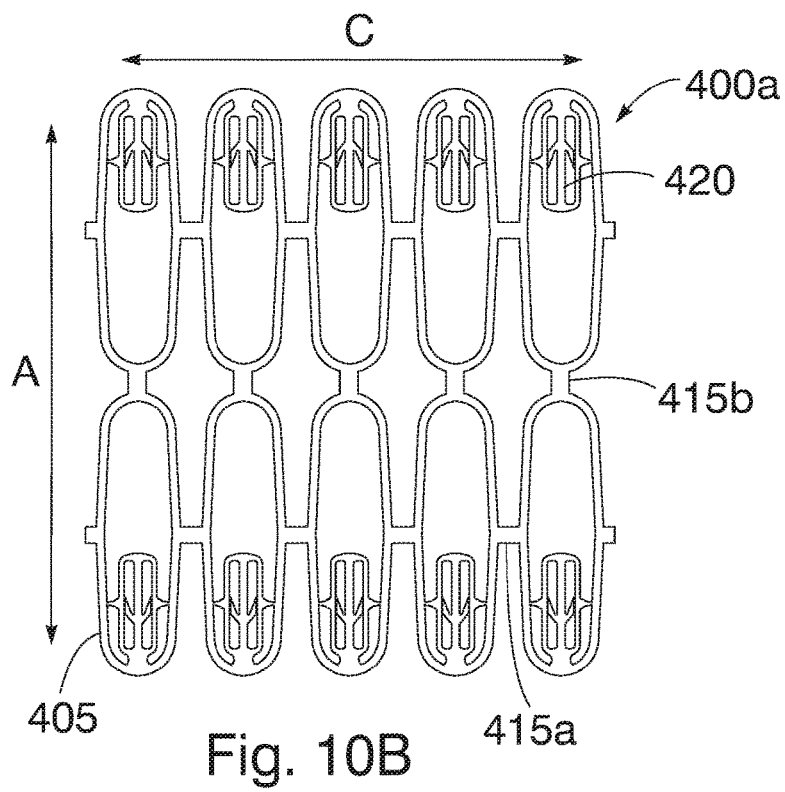
FIG. 10B is a plan view of the stent form of FIG. 10A.

Referring now to FIGS. 10A and 10B, there is shown a fourth embodiment of the stent 400. In the fourth embodiment, the stent 400 is formed of an m×n array 400a of ovals 405. With reference to FIG. 10B, the array 400a of ovals 405 can be formed by laser-cutting a sheet or tube of metal, preferably stainless steel. Adjacent ovals 405 are connected to each other in the circumferential direction C by connectors 415a and in the axial direction A by connectors 415b positioned between the ovals coincident with their common short and long axes, respectively.

At least some of the ovals 405 at the ends of the stent 400 (that is, the ovals 405 in rows 1 and n in the axial direction) have a prong 420 extending inwardly from their outer ends in approximate alignment with their longitudinal axes. The prongs 420 are placed in facing pairs extending from ovals 405 that are in alignment in the axial direction A.

Figure 10C:
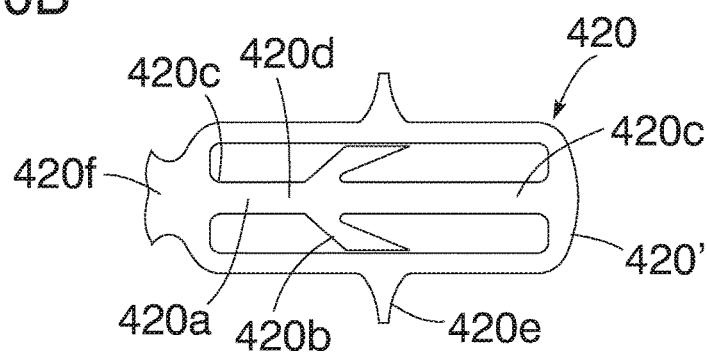
FIG. 10C is an enlarged view of the prong of the stent of FIG. 10A.

As shown in FIG. 10C, each prong 420 has substantially the same configuration as an oval 305 and a prong 320 of the third embodiment, described above. That is, each prong 420 includes an oval frame 420', a spine 420a extending the length of the long axis of the oval frame 420', and a furcation 420b on either side of the spine 420a at a location between the ends of the spine 420. The spine 420a has two end hinge points 420c at the ends thereof and one intermediate hinge point 420d at the base of the furcations 420b.

The oval frames 420' are connected at their short axes to the ovals 405 by connectors 420e, and are connected at one end of their long axes to the ovals 405 by a connector 420f. Thus, as the ovals 405 foreshorten, the oval frames 420' also foreshorten. The amount by which the oval frames 420' are foreshortened and the angle of the furcations 420b can be adjusted by varying the location of the furcations 420b and the intermediate hinge point 420d relative to the ends of the spines 420 and the end hinge points 420c. Preferably, the prongs 420 are formed by laser cutting.

As with stent 300, stent 400 is loaded over the balloon 130 of a conventional balloon catheter 132 and inserted into the artery or other body cavity according to conventional medical procedure. As the balloon 130 inflates, the ovals 405 and the oval frames 420' foreshorten in the axial direction, causing the spines 420a of the prongs 420 to bend at the hinges 420c and 420d and the consequent activation of the prongs 420. As the balloon 130 continues to inflate, the angles assumed by the spines 420a at their hinges reach their maximums, bringing opposing furcations 420b together to engage the tissue therebetween.

There may be intervening "blank" ovals 405 without any prongs 420, and which serve merely as spacers. The blank ovals 405 are utilized in some situations where more space is required between the connecting prongs 420. At least some of the ovals 405 at one end of the stent 400 can include a docking socket (not shown) similar to the docking socket 360 shown in FIG. 8C, for mating to the cardiac locking pin of a valve frame.

Modifications and variations of the above-described embodiments of the present invention are possible, as appreciated by those skilled in the art in light of the above teachings. It is therefore to be understood that the invention may be practiced otherwise than as specifically described.

What is claimed is:

1. A method of deploying a percutaneous heart valve into a body cavity having an opening surrounded by surrounding body tissue, the method comprising:

delivering a percutaneous heart valve to the body cavity in a collapsed configuration, the percutaneous heart valve comprising:
  an expandable frame comprising a proximal end and a distal end and a longitudinal axis extending therethrough, the expandable frame comprising a plurality of cells configured to permit the frame to radially expand and collapse between the collapsed configuration and an expanded configuration;
  a valve seated inside the expandable frame;
  a proximal anchoring portion; and
  a distal anchoring portion comprising a plurality of distal anchors; and
radially expanding the expandable frame to the expanded configuration within the opening, wherein, when the percutaneous heart valve is in the expanded configuration:
  the proximal anchoring portion extends at least partially distally;
  at least a portion of each distal anchor extends proximally to a proximalmost portion of the distal anchor positioned radially outward from the frame, the proximalmost portions extending in a direction that is more parallel with the longitudinal axis than with a transverse axis perpendicular to the longitudinal axis;
  at least one of the plurality of distal anchors bends radially outwardly before bending to extend toward the proximal anchoring portion; and
  the proximalmost portions of the plurality of distal anchors are spaced apart by less than two cell lengths from a distalmost portion of the proximal anchoring portion;
wherein radially expanding the expandable frame draws the proximal anchoring portion and the plurality of distal anchors closer together with the surrounding body tissue positioned between the proximal anchoring portion and the plurality of distal anchors.

2. The method of claim 1, wherein:
when the frame is in the expanded configuration within the opening, the proximal anchoring portion is positioned on a first side of the surrounding body tissue and the distal anchors are positioned on a second side of the surrounding body tissue opposite the first side; and
upon movement of the frame within the opening in a proximal direction, the distal anchors longitudinally engage the second side of the surrounding body tissue with a proximally-facing surface of the proximalmost portions of the distal anchors which are positioned radially outward from the frame.

3. The method of claim 1, wherein, when the frame is in the expanded configuration within the opening:
the proximal anchoring portion is positioned on a first side of the surrounding body tissue and the distal anchors are positioned on a second side of the surrounding body tissue opposite the first side; and
the proximalmost portions of the distal anchors engage the second side of the surrounding body tissue at a location radially outward of the opening.

4. The method of claim 1, wherein the proximal anchoring portion comprises a plurality of circumferentially spaced anchoring tips positioned radially outward from the frame when the frame is in the expanded configuration.

5. The method of claim 4, wherein when the frame is in the expanded configuration within the opening, the plurality of circumferentially spaced anchoring tips of the proximal anchoring portion extend at least partially distally toward a first side of the surrounding body tissue.

6. The method of claim 1, further comprising forming the cells, the proximal anchoring portion, and the distal anchoring portion by laser cutting.

7. The method of claim 1, wherein each of the plurality of distal anchors are connected to distal ends of cells of the frame.

8. The method of claim 7, wherein, when the frame is in the expanded configuration, the distal ends of each cell to which the distal anchors are attached are in a position spaced radially outward relative to a portion of the frame located proximal to the distal ends of each cell to which the distal anchors are attached.

9. The method of claim 7, wherein, when the frame is in the expanded configuration, the plurality of distal anchors bend radially outwardly to a position spaced radially outward relative to a portion of the frame located proximal to the distal ends of the cells to which the distal anchors are attached, the at least one distal anchor being attached to the distal end of the cell, at least a portion of the at least one distal anchor extending generally parallel to the longitudinal axis.

10. The method of claim 1, wherein a distalmost portion of the proximal anchoring portion and the proximalmost portions of the plurality of distal anchors are sized to pinch first and second sides of the surrounding body tissue together after the radially expanding.

11. The method of claim 1, wherein the body cavity comprises a native aortic valve.

12. A method of deploying a percutaneous heart valve within a body cavity having an opening surrounded by surrounding body tissue, the method comprising:
delivering a percutaneous heart valve to the body cavity in a collapsed configuration, the percutaneous heart valve comprising:
  an expandable frame comprising a proximal end and a distal end and a longitudinal axis extending therethrough, the expandable frame comprising a plurality of cells configured to permit the frame to radially expand and collapse for deployment within the opening of the body cavity between the collapsed configuration and an expanded configuration;
  a valve seated inside the expandable frame;
  a proximal anchoring portion; and
  a distal anchoring portion comprising a plurality of distal anchors, each distal anchor comprising an attached end connected to the frame, a free end, and a bend between the attached end and the free end; and
radially expanding the expandable frame to the expanded configuration within the opening, wherein, when the percutaneous heart valve is in the expanded configuration:
  the proximal anchoring portion extends at least partially distally;
  at least a portion of each distal anchor extends proximally to a proximalmost portion of the distal anchor positioned radially outward from the frame, the proximalmost portions extending in a direction that is more parallel with the longitudinal axis than with a transverse axis perpendicular to the longitudinal axis; and
  the proximalmost portions of the distal anchors are spaced apart by less than two cell lengths from a distalmost portion of the proximal anchoring portion;

wherein the radially expanding the expandable frame draws the proximal anchoring portion and the distal anchors closer together with the surrounding body tissue positioned between the proximal anchoring portion and the plurality of distal anchors.

13. The method of claim 12, wherein, when the frame is in the expanded configuration, at least a portion of the distal anchors between the attached end and the bend extends radially outward.

14. The method of claim 13, wherein, when the frame is in the expanded configuration, each bend orients a portion of the distal anchor immediately after the bend in a direction more parallel with the longitudinal axis than a portion of the distal anchor immediately before the bend.

15. The method of claim 12, wherein:
when the frame is in the expanded configuration within the opening, the proximal anchoring portion is positioned on a first side of the surrounding body tissue and the distal anchors are positioned on a second side of the surrounding body tissue opposite the first side; and
upon movement of the frame within the opening in a proximal direction, the plurality of distal anchors longitudinally engage the second side of the surrounding body tissue with a proximally-facing surface of the proximalmost portions of the distal anchors which are positioned radially outward from the frame.

16. The method of claim 12, wherein, when the frame is in the expanded configuration within the opening:
the proximal anchoring portion is positioned on a first side of the surrounding body tissue and the plurality of distal anchors are positioned on a second side of the surrounding body tissue opposite the first side; and
the proximalmost portions of the plurality of distal anchors engage the second side of the surrounding body tissue at a location radially outward of the opening.

17. The method of claim 12, wherein the proximal anchoring portion comprises a plurality of circumferentially spaced anchoring tips positioned radially outward from the frame when the frame is in the expanded configuration.

18. The method of claim 17, wherein when the frame is in the expanded configuration within the opening, the plurality of circumferentially spaced anchoring tips of the proximal anchoring portion extend at least partially distally toward a first side of the surrounding body tissue.

19. The method of claim 12, wherein the body cavity comprises a native aortic valve.

* * * * *